US005571177A

United States Patent [19]
Deacon et al.

[11] Patent Number: 5,571,177
[45] Date of Patent: Nov. 5, 1996

[54] IOL STRUCTURED FOR POST-OPERATIVE RE-POSITIONING AND METHOD FOR POST-OPERATIVE IOL RE-POSITIONING

[75] Inventors: Jim Deacon, Capistrano Beach; Glenn R. Sussman, Lake Forest; Joseph I. Weinschenk, III, Laguna Niguel, all of Calif.

[73] Assignee: Allergan, Irvine, Calif.

[21] Appl. No.: 77,810

[22] Filed: Jun. 14, 1993

[51] Int. Cl.$^6$ .................................................. A61F 2/16
[52] U.S. Cl. ............................................................ 623/6
[58] Field of Search .................................................. 623/6

[56] References Cited

U.S. PATENT DOCUMENTS

| | | | |
|---|---|---|---|
| 4,134,161 | 1/1979 | Bayers | 623/6 |
| 4,136,466 | 1/1979 | Wrue . | |
| 4,219,721 | 8/1980 | Kamen et al. . | |
| 4,403,354 | 9/1983 | Rainin | 623/6 |
| 4,435,855 | 3/1984 | Pannu | 623/6 |
| 4,443,441 | 4/1984 | Galin . | |
| 4,463,457 | 8/1984 | Kelman | 623/6 |
| 4,575,373 | 3/1986 | Johnson | 623/6 |
| 4,585,456 | 4/1986 | Blackmore | 623/6 |
| 4,617,023 | 10/1986 | Peyman | 623/6 |
| 4,642,113 | 2/1987 | Dubroff | 623/6 |
| 4,661,109 | 4/1987 | White | 623/6 |
| 4,662,882 | 5/1987 | Hoffer | 623/6 |
| 4,666,445 | 5/1987 | Tillay | 623/6 |
| 4,676,793 | 6/1987 | Bechert, II | 623/6 |
| 4,681,585 | 7/1987 | Sayano et al. | 623/6 |
| 4,685,921 | 8/1987 | Peyman | 623/6 |
| 4,685,922 | 8/1987 | Peyman | 623/6 |
| 4,781,718 | 11/1988 | Lindstrom | 623/6 |
| 4,834,753 | 5/1989 | Sulc et al. | 623/6 |
| 4,872,876 | 10/1989 | Smith | 623/6 |
| 4,946,470 | 8/1990 | Sulc et al. | 623/6 |
| 5,108,429 | 4/1992 | Wiley | 623/6 |
| 5,147,395 | 9/1992 | Willis | 623/6 |
| 5,269,813 | 12/1993 | Yoshida et al. | 623/6 |
| 5,288,293 | 2/1994 | O'Donnell, Jr. | 623/6 |

FOREIGN PATENT DOCUMENTS

| | | |
|---|---|---|
| 0094158 | 11/1983 | European Pat. Off. . |
| 478929 | 11/1983 | European Pat. Off. . |
| 0278724 | 8/1988 | European Pat. Off. . |
| 0336318 | 10/1989 | European Pat. Off. . |
| 1424828 | 9/1988 | U.S.S.R. . |
| WO8701931 | 4/1987 | WIPO . |
| 9007914 | 7/1990 | WIPO ........................................ 623/6 |

OTHER PUBLICATIONS

Friedberg et al, A new technique for repositioning and fixating a dislocated intraocular lens, Arch Ophthalmol, Mar. 1992, 110 (3) pp. 413–415 Abstract Only.

Chan, An improved technique for management of dislocated posterior chamber implants, Ophthalmology, Jan. 1992, 99 (1) pp. 51–57 Abstract Only.

Bowman et al, Noninvasive repositioning of a posterior chamber intraocular lens following pupillary capture, J Cataract Refract Sur, Nov. 1991, 17 (6) pp. 843–847 Abstract Only.

Flynn et al, Management of subluxated and posteriorly dislocated intraocular lenses using pars plana vitrectomy instrumentation, J Cataract Refract Surg, Jan. 1990, 16 (1) pp. 51–56 Abstract Only.

Smiddy, Dislocated posterior chamber intraocular lens. A new technique of management, Arch Ophthalmol, Nov. 1989, 107 (11) pp. 1678–1680 Abstract Only.

Neumann et al, Complications associated with STAAR silicone implants, J Cataract Refract Surg, Nov. 1987, 13 (6) pp. 653–656 Abstract Only.

(List continued on next page.)

*Primary Examiner*—Mary Beth Jones
*Attorney, Agent, or Firm*—Frank J. Uxa

[57] ABSTRACT

A new intraocular lens (IOL) is disclosed. In one embodiment, this IOL comprises an optic and, secured to the optic, a fixation member including at least one alterable portion structured to be altered after the intraocular lens is placed in an eye to at least assist in controllably repositioning the optic in the eye.

13 Claims, 2 Drawing Sheets

OTHER PUBLICATIONS

Stark et al, Management of posteriorally dislocated intraocular lenses, Ophthalmic Surg. Aug. 1980, 11 (8) pp. 495–497 Abstract Only.

Poley et al, A closed technique for repositioning dislocated iris plane lenses, J Am Intraocul Implant Soc Oct. 1979, 5 (4) pp. 316–320 Abstract Only.

Praeger, Praeger micro irrigating hook intraocular lens implantation, Ophthalmic Surg. Jul. 1979, 10(7) pp. 30–32 Abstract Only.

Corcoran, Spontaneous repositioning of a dislocated Medallion intraocular lens, J Am Intraocul Implant Soc. Nov. 1985, 11 (6) pp. 598–599 Abstract Only.

Moretsky, Suture fixation technique for subluxated posterior chamber IOL through stab wound incision, J Am Intraocul Implant Soc Fall 1984, 10 (4) pp. 477–480 Abstract Only.

Wand et al, Thymoxamine hydrochloride:an alpha–adrenergic blocker, Sury Ophthalmol Sep.–Oct. 1980, 25 (2) pp. 75–84 Abstract Only.

Flynn, Pars plana vitrectomy in the management of subluxed and posteriorly dislocated intraocular lenses, Graefes Arch Clin Exp Ophthalmol 1987, 225(3) pp. 169–172 Abstract Only.

Nevyas et al, A YAG laser technique to facilitate removal of posterior chamber intraocular lenses from the capsular bag, J Cataract Refract Surg Mar. 1987, 13 (2) pp. 201–204 Abstract Only.

Sternberg et al, Treatment of dislocated posterior chamber intraocular lenses, Arch Ophthalmol Sep. 1986, 104 (9) pp. 1391–1393 Abstract Only.

Ayaki et al, Histopathologic study of after cataract in the pseudophakic rabbit eye using out–of–the–bag fixation, Nippon Ganka Gakkai Zasshi Jun. 1990, 94(6) pp. 553–558 (I) Abstract Only.

Lyons et al, Report of a repositioned posteriorly dislocated intraocular lens via pars plicata sclerotomy, J Cataract Refract Surg Jul. 1990 16(4) pp. 509–511 (Abstract Only).

Nabors et al, Ciliary sulcus suturing of a posterior chamber intraocular lens, Ophthalmic Surg. Apr. 1990 21 (4) pp. 263–265 (Abstract Only).

Smiddy et al, Management of dislocated posterior chamber intraocular lenses, Ophthalmology Jun. 1991, 98 (6) pp. 889–894 (Abstract Only).

Bloom et al, Scleral fixation suture for dislocated posterior chamber intraocular lens, Ophthalmic Surg, Dec. 1990, 21 (12) pp. 851–854 (Abstract Only).

Ayaki et al, Histopathologic study of after–cataract in the pseudophakic rabbit eye using in–the–bag fixation, Nippon Ganka Gakkai Zasshi, Jun. 1990, 94 (6) pp. 559–565 (II) (Abstract Only).

Biedner et al, Subconjunctival dislocation of intraocular lens implant, Am J Ophthalmol Aug. 1977, 84 (2) pp. 265–266 (Abstract Only).

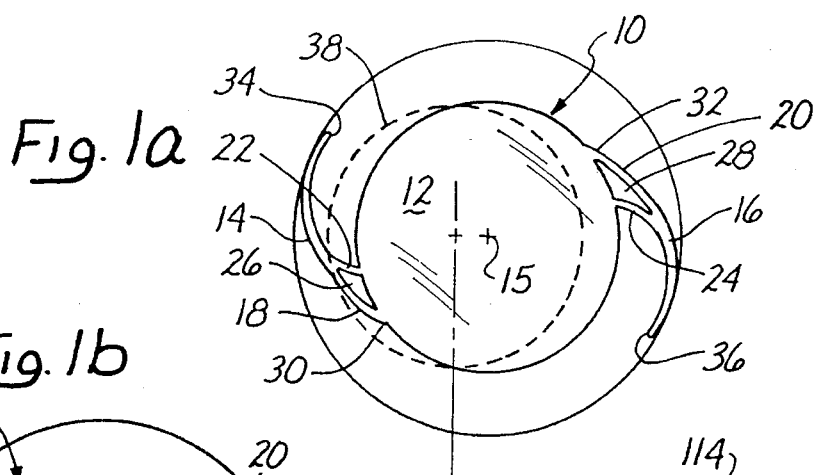
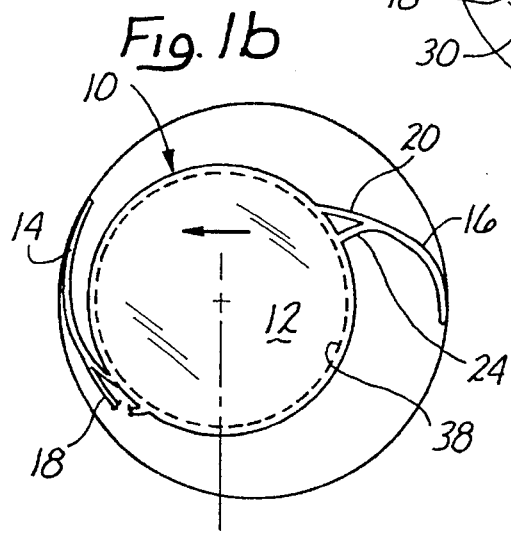
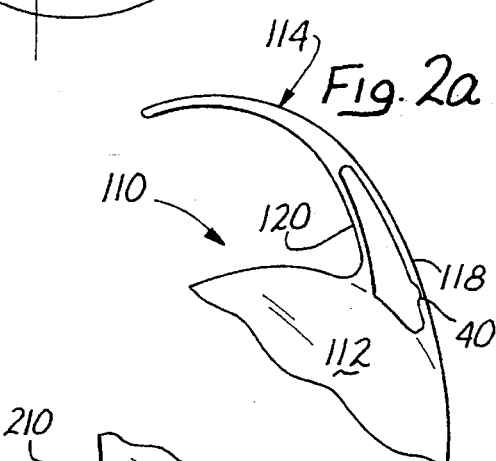
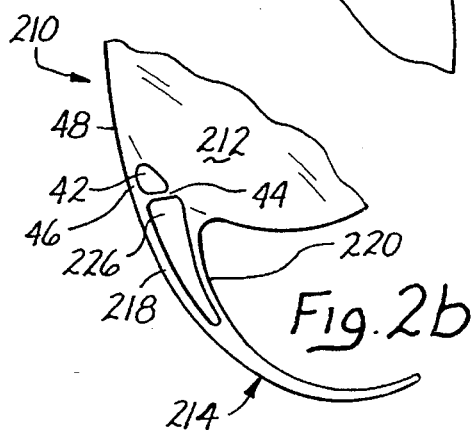
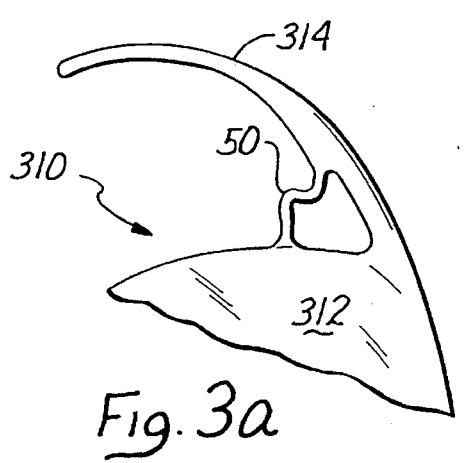
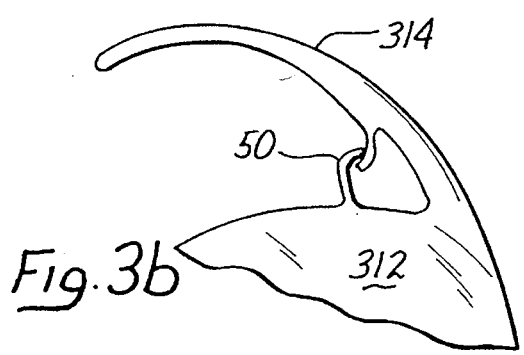

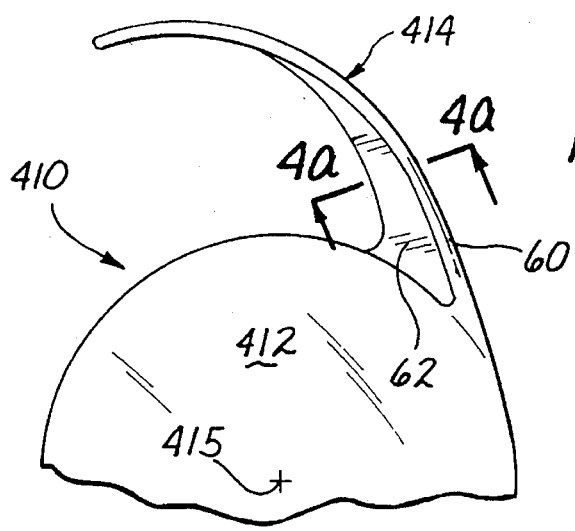
Fig. 4
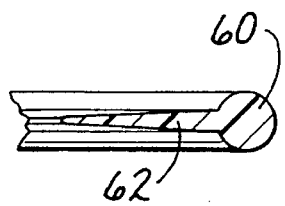
Fig. 4a
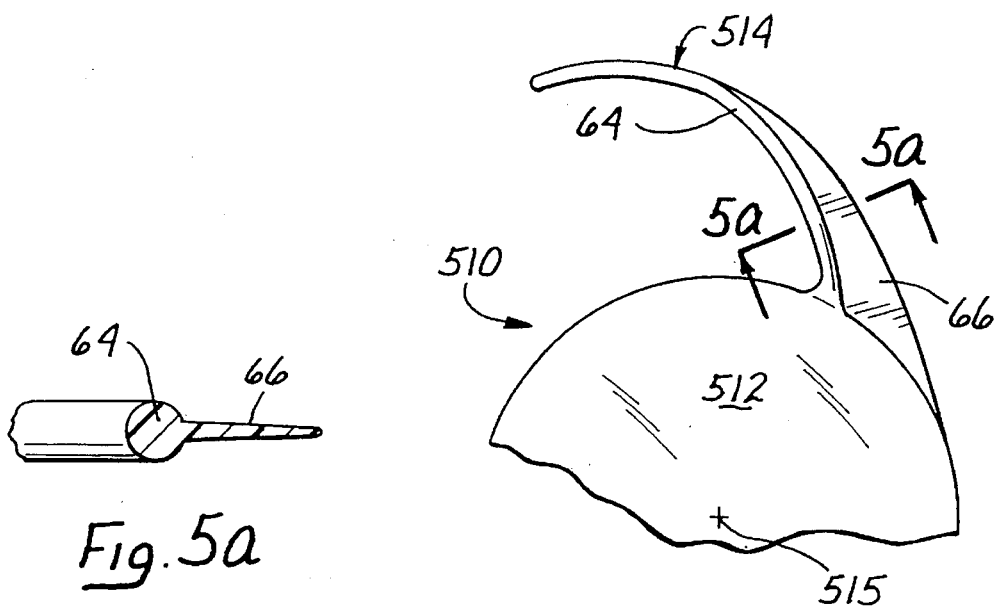
Fig. 5a
Fig. 5
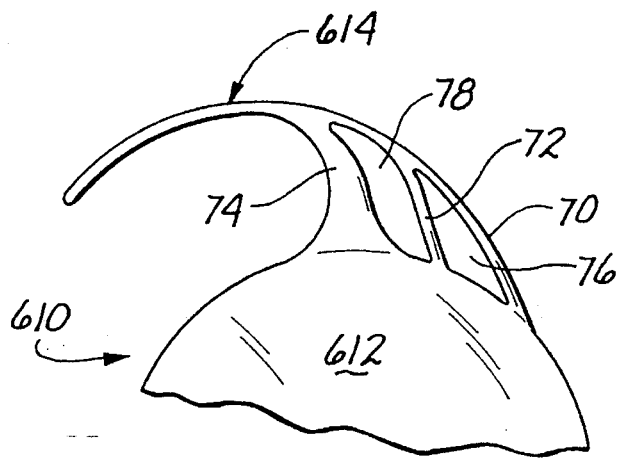
Fig. 6

IOL STRUCTURED FOR POST-OPERATIVE RE-POSITIONING AND METHOD FOR POST-OPERATIVE IOL RE-POSITIONING

BACKGROUND OF THE INVENTION

This invention relates to intraocular lenses (IOLs) structured to be re-positioned after being placed in an eye and to methods for repositioning IOLs in the eye.

The vision impairing disease, known as cataract, can be alleviated by surgically replacing the natural lens of the eye with an artificial IOL. Such an IOL may be inserted in the eye by a variety of well known surgical procedures. However, once the IOL is placed in the eye, it is often found that the IOL optic is or becomes decentered or otherwise moves to a less-than-optimal position in the eye.

IOLs, for example, IOLs located in the anterior chamber or posterior chamber of the eye, which are not optimally positioned in the eye or centered on the visual axis of the eye are prone to a variety of optical and physical problems, such as optical distortion, edge glare, second images, reduction in multifocal effect (in some designs) and the like. In addition, posterior chamber opacification may be altered or encouraged by a decentered IOL. Decentration has been reduced by use of continuous capsulorhexis techniques and bag placement, but has not been eliminated. Further, the smaller diameter IOL optics increasingly used today tend to require more precise positioning and to be more sensitive to relatively minor amounts of mal-positioning than their larger diameter predecessors. Even a perfectly positioned IOL may move slightly as remnant lens epithelial cells fill in the capsule.

Repositioning an IOL by mechanical means after IOL implantation is an invasive procedure involving reopening the eye and working behind the iris. In extreme cases, IOL removal may be indicated. Aside from the disadvantages of the surgical procedure itself, possible further complications include inflammation, infection, pigmentary dispersion and endothelial damage.

It would be advantageous to provide a system for repositioning an IOL after it has been placed in the eye without requiring such invasive surgical techniques.

SUMMARY OF THE INVENTION

IOLs structured to be post-operatively repositioned and methods for such post-operative repositioning of IOLs have been discovered. The present IOLs are structured to allow repositioning, for example, in the coronal plane, by the use of energy, such as a laser beam, passed into the eye, for example, through ere pupil of the eye, and/or by the use of one or more other non-invasive techniques. This approach allows the surgeon to properly position the IOL optic, for example, center the optic relative to the pupil or to the optical or visual axis, in the eye either immediately following surgery or later, as required. Further, most ophthalmologists already have access to and experience with lasers. Therefore, the use of lasers in accordance with the present invention requires little or no additional surgeon training. Moreover, the present system is very effective in positioning IOLs with small diameter optics. The present IOLs can be produced on existing automated machinery. Manufacturing costs, implantation procedures etc. are substantially equivalent to current products and procedures.

In one broad aspect, the present invention is directed to an IOL comprising an optic and, secured to the optic, a fixation member, preferably a plurality of such fixation members. The optic functions in a manner similar to a conventional optic of a conventional IOL. Similarly, the fixation member or members (haptics) function in a manner similar to the fixation members or haptics of a conventional IOL. In the present IOLs, the fixation member includes at least one alterable portion structured to be altered, preferably non-surgically altered, after the IOL is placed in an eye to at least assist in controllably repositioning the optic in the eye. Thus, the present IOLs include a fixation member or members with one or more alterable portions specifically structured and designed to be altered to provide for a controlled repositioning of the optic in the eye. The present IOLs are preferably structured to allow the optic to be moved in a substantially predictable, more preferably a substantially predetermined, manner to provide substantial control of the positioning of the IOL in the eye. In one particularly useful embodiment, the fixation member of the IOL requiring repositioning is exposed through the pupil of the eye. When sufficient repositioning of the optic has been achieved, this fixation member no longer is exposed through the pupil so that the repositioning is self limiting and relatively fail safe.

In another broad aspect of the present invention, methods for repositioning an IOL in situ in an eye are provided and comprise altering, preferably altering non-surgically, the configuration of an IOL comprising an optic and a fixation member located in an eye. More preferably, this altering includes passing energy, still more preferably energy from a laser beam, into the eye, for example, through the pupil of the eye.

As used herein, the term "non-surgically" means that the IOL is repositioned without being physically contacted by any mechanical device, such as a conventional knife and/or other mechanical surgical instrument. In the event an incision in the eye is made to facilitate the IOL repositioning in accordance with the present invention, it is preferred that such incision have a size of less than about 0.5 mm or less than about 1 mm. Incisions of this size are substantially smaller than those conventionally required to surgically reposition IOLs, cause little or no trauma and require little or no healing time before the patient can conduct or perform normal activities.

The invention, together with additional features and advantages thereof, may best be understood by reference to the following description taken in connection with the accompanying illustrative drawings.

BRIEF DESCRIPTION OF THE DRAWINGS

FIG. 1a is a schematic illustration of an IOL in accordance with the present invention decentered relative to the pupil in an eye.

FIG. 1b is a schematic illustration of the IOL shown in FIG. 1a after its configuration has been altered, showing such altered IOL to be properly centered relative to the pupil in the eye.

FIG. 2a is a partial plan view of an additional embodiment of an IOL in accordance with the present invention.

FIG. 2b is a partial plan view of a further embodiment of an IOL in accordance with the present invention.

FIG. 3a is a partial plan view of another embodiment of an IOL in accordance with the present invention.

FIG. 3b is a partial plan view of the IOL shown in FIG. 3a after its configuration has been altered.

FIG. 4 is a partial plan view of yet another embodiment of an IOL in accordance with the present invention.

FIG. 4a is a view taken generally along line 4a—4a of FIG. 4.

FIG. 5 is a partial plan view of a still further embodiment of an IOL in accordance with the present invention.

FIG. 5a is a view taken generally along line 5a—5a of FIG. 5.

FIG. 6 is a partial plan view of a further additional IOL in accordance with the present invention.

DETAILED DESCRIPTION OF THE INVENTION

FIG. 1a shows an IOL in accordance with the present invention placed in the eye and decentered relative to the pupil of the eye. Thus, this IOL, shown generally at 10, includes an optic 12 and two diametrically opposed fixation members 14 and 16 which are secured to and extend radially outwardly from optic 12. IOL 10, which includes an optical axis 15, is made of a single piece of polymeric material, for example, polymethylmethacrylate (PMMA). However, IOLs made from two, three or more pieces of material, for example, different materials, are also included within the scope of the present invention.

Each of the optic 12 and fixation members 14 and 16 of IOL 10 functions in the eye in a manner similar to corresponding components of a conventional IOL. Thus, the optic 12 acts as the lens body of IOL 10 and is optically clear. Optic 12 provides the required lens capabilities (focusing/vision correction) of IOL 10. Each of the fixation members 14 and 16 acts to fix and hold IOL 10 in the eye and to be secured to and/or abut the ocular tissue surrounding the IOL.

Each of the fixation members 14 and 16 includes a first arm 18 and 20, respectively, and a second arm 22 and 24, respectively. Hollow or through (open) spaces 26 and 28 separate the first and second arms of fixation members 14 and 16, respectively. Also, the first and second arms and hollow space of each of the fixation members 14 and 16 are located closer to the proximal end 30 and 32, respectively, of the fixation member than to the distal end 34 and 36, respectively, of the fixation member. This feature provides for more movement of optic 12 upon the altering (e.g., breaking) of the first or second arms of the fixation members. The first and second arms of each of the fixation members 14 and 16 are sufficiently thin that such arms can be broken by the energy emitted from a conventional laser, for example, a ND-YAG laser.

The IOL 10 can be implanted into a mammalian eye, for example, a human eye, using conventional and well known surgical techniques, such as techniques which are commonly used to implant conventional IOLs. In general, an incision is made in the eye and the natural lens is removed, for example, using a conventional phacoemulsification procedure. With the lens capsule vacated, the IOL 10 is introduced into the eye, such as into the posterior chamber of the eye, and is positioned and fixed within the eye. The incision is then repaired. After healing, the IOL 10 implanted in the eye is effective to provide vision correction to the recipient of the IOL. The present invention is also applicable to IOLs structured for placement within the anterior chamber of the eye. Such anterior chamber IOLs are within the scope of the present invention.

The IOL 10 can be, or over a period of time can become, decentered relative to the pupil 38 of the eye, as shown in FIG. 1a. The IOL 10 may be centered relative to the eye structure supporting the IOL and still be decentered relative to the pupil, for example, if the supporting structure is decentered relative to the pupil, as shown in FIG. 1a. If this condition is left as is, IOL 10 becomes substantially less effective to provide proper vision to the patient. Optical distortion, glare, and/or other possible problems exist when IOL 10 is decentered as in FIG. 1a. In the decentered position, first and second arms 18 and 22 of fixation member 14 are exposed through pupil 38. This is one indication that the IOL 10 is decentered. Also, because portions of fixation member 14 are exposed through the pupil 38, fixation member 14 (and not fixation member 16) is to be altered to reposition IOL 10. This feature is very effective in identifying which fixation member (the fixation member exposed through the pupil) is to be altered in accordance with the present invention.

To reposition IOL 10, for example, in the coronal plane, a laser beam from a conventional ND:YAG laser is passed through the pupil 38 of the eye to break the first arm 18 of fixation member 14. This broken first arm 18, as shown in FIG. 1b, controllably weakens fixation member 14 which, in turn, causes optic 12 to move to the left or toward fixation member 14, as shown in FIG. 1b, to recenter optic 12 relative to pupil 38. As shown in FIG. 1b, after first arm 18 of fixation member 14 is broken, optic 12 moves so that substantially no portion of fixation member 14 (or fixation member 16) is exposed through pupil 38. This is an indication that the repositioning has been successful and that no further alteration of IOL 10 is needed. The pupil 38 may be dilated prior to passing the laser beam through it.

The breaking of first arm 18 of fixation member 14 occurs without invasively reopening the eye, preferably without physically contacting IOL 10 with any mechanical surgical instrument, in particular, by passing energy, such as in the form of a laser beam, through the pupil 30 to effect the breaking of this first arm. In this manner, the recentered IOL 10 is substantially immediately ready for normal use, and the patient (and the eye) suffers substantially no surgical trauma and requires substantially no healing time before resuming normal activities. The technique used to reposition optic 12 in the eye should, of course, cause no significant detrimental effect on the IOL 10, on the eye in which the IOL is located or on the recipient of the IOL.

While FIG. 1b illustrates that first arm 18 of fixation member 14 is broken to reposition IOL 10 in the eye, a similar procedure can be used to break second arm 22 (rather than first arm 18) of fixation member 14. Also, if needed to reposition optic 12, first arm 20 or second arm 24 of fixation member 16 could be broken, preferably non-surgically broken. It is preferred that each of the fixation members include a plurality of alterable portions, such as first arm 18 and second arm 22. Each of the plurality of alterable portions is preferably structured to be altered to provide a different, more preferably substantially predetermined, amount of repositioning of the optic in the eye. This provides a great deal of flexibility in controllably repositioning the optic in the eye.

In another embodiment, which is also illustrated by FIG. 1a, the fixation members 14 and 16 (or the first arms 18 and 20) are made of a polymeric material, herewith referred to as "Tg material", which has a glass transition temperature, Tg, at least about 40° C., for example, 50° C. The fixation members 14 and 16 (or the first arms 18 and 20) are originally manufactured in either a straight or highly curved configuration. During this manufacture, the components made of the "Tg material" are heated above the glass transition temperature, bent to the desired shape, and then physically held in that shape while being cooled below the Tg. This can be done before or after the fixation members 14 and 16 are secured to optic 12.

In this embodiment, the fixation member (or part thereof) is heated, for example, by passing radiant energy through the pupil of the eye, to heat the fixation member (or part thereof) to a temperature above the Tg to recenter the optic. For example, with specific reference to FIG. 1a, second arm 22 of fixation member 14 is made of Tg material originally manufactured in a highly curved configuration. By heating this part to above its glass transition temperature, to above 50° C. (by passing radiant energy, for example, from a thin probe tip passed into the eye through a "pin-size" incision having a size of no more than about 0.2 mm and positioned immediately adjacent or in contact with this part), second arm 22 returns to its highly curved configuration, thereby causing optic 12 to move left and to be centered relative to the pupil 38 of the eye.

In another embodiment, the fixation member (or part thereof) is made of Tg material which has no specific "memory" based on its manufacturing history (such as the Tg material described in the two immediately preceding paragraphs). By heating such a fixation member (or part thereof) while it is under compression in the eye to a temperature above Tg, the fixation member (or part thereof) temporarily softens so that the fixation member is further bent or compressed, moving the optic of the IOL in the eye. For example, with specific reference to FIG. 1a, second arm 22 of fixation member 14 is made of such a Tg material. By heating this part to above its glass transition temperature, to above 50° C. (for example, as described above), second arm 22 temporarily softens, thereby causing fixation member 14 to further bend or compress. This, in turn, causes optic 12 to move left and be centered relative to the pupil 38 of the eye.

The optics of the present IOLs may be constructed of any suitable material or combination of materials. Such materials include, for example, silicon-based polymeric materials, acrylic polymeric materials, such as PMMA and the like, hydrogel-forming polymers and the like, other polymeric materials, glass and mixtures thereof.

The fixation members can be of various constructions, configurations, and materials. For example, the fixation members may be constructed of PMMA or polypropylene or the like materials. The fixation members are preferably made of polymeric materials. The fixation members can be, and preferably are made of the same material as the optics, and more preferably are unitary and integral with the optics. Preferably, the fixation members are coupled to the optic at generally diametrically opposed locations, for example, secured to the lens body at generally diametrically opposed locations.

With reference to FIG. 2a, an additional IOL, shown generally as 110 includes an optic 112 and a fixation member 114. Except as expressly stated herein, each of the components of additional IOL 110 is structured and is sized and functions in a manner similar to the corresponding component of IOL 10. The reference numerals of the corresponding components of additional IOL 110 are increased by 100 relative to the reference numerals of the corresponding components of IOL 10.

Because of the partial view of IOL 110 shown, the other fixation member, which is located diametrically opposed to fixation member 114, is not shown. This other fixation member can have the same configuration as fixation member 114 or can be configured differently than fixation member 114. Moreover, the other fixation member need not be structured so as to be non-surgically alterable in accordance with the present invention. (This paragraph applies with equal weight to each of the IOLs shown in FIGS. 2a, 2b, 3a, 3b, 4, 4a, 5, 5a and 6.)

The primary difference between fixation member 114 and fixation member 14 involves an area or target of first arm 118 identified as 40. Area 40 has a reduced thickness relative to the overall or general thickness of the first arm 118. This area 40 is more easily altered or broken, for example, by a laser beam, than is the first arm 118 in general. Moreover, the area 40 can be considered to be a target area in that by breaking first arm 118 at area 40, a predictable, and preferably substantially predetermined, amount of movement or repositioning of optic 112 can be obtained. In this manner, area 40 facilitates the ease and controllability of moving or repositioning optic 112 by breaking first arm 118. It should be noted that more than one reduced thickness or target area, such as area 40, can be included in first arm 118. Alternately, or in addition, one or more such reduced thickness or target areas can be included along the length of second arm 120 and/or along the length of any or all of the other fixation member alterable portions described herein.

With regard to FIG. 2b, a further IOL 210 is provided which includes an optic 212, a fixation member 214, a first arm 218, a second arm 220 and a second hollow space 42. Except as expressly stated herein, each of the components of further IOL 210 is structured and is sized and functions in a manner similar to the corresponding component of IOL 10. The reference numerals of the corresponding components of further IOL 210 are increased by 200 relative to the reference numerals of the corresponding components of IOL 10.

The primary differences between IOL 210 and IOL 10 are the presence of a second hollow or through (open) space 42 which is located separate from hollow space 226, the region 44 located between first hollow space 226 and the second hollow space, and the peripheral region 46 between the second hollow space and the periphery 48 of IOL 210. If peripheral region 46 is broken, region 44 advantageously acts to retain first arm 218 so as to prevent the end of the first arm (at the broken peripheral region 46) from extending outwardly and interfering with surrounding ocular tissue. Also, the region 44 located between first hollow space 226 and second hollow space 42 can be broken to provide for an additional degree of control over the repositioning of optic 212.

The embodiment shown in FIG. 2b is illustrative of preferred embodiments of the present invention in which a plurality of alterable portions are included to provide the surgeon with alternative target sites for repositioning the optic of an IOL in accordance with the present invention. By selectively choosing the target site to break, the overall stiffness of fixation member 214 can be controllably varied so as to more effectively control the repositioning of optic 212, for example, to satisfy the repositioning requirements of the particular situation at hand.

In FIGS. 3a and 3b, a particularly useful embodiment of the present invention is shown with regard to another IOL 310. Except as expressly stated herein, each of the components of another IOL 310 is structured and is sized and functions in a manner similar to the corresponding components of IOL 10. The reference numerals of the corresponding components of another IOL 310 are increased by 300 relative to the reference numerals of the corresponding components of IOL 10.

The primary difference between IOL 310 and IOL 10 is the configuration of arm 50. In a typical situation in the eye, the fixation member 314 is present under compression. Arm 50 is configured and structured to be under tension when fixation member 314 overall is under compression. Thus, when it is desired to reposition optic 312, a laser beam can be passed through the pupil of the eye to break arm 50. This arm 50, as shown in FIG. 3b, because it is under tension, breaks so as to have overlapping ends. This is very advantageous since it prevents the severed ends from interfering with one another. By breaking arm 50, fixation member 314 is weakened thereby allowing optic 312 to be controllably repositioned.

Reference is now made to FIGS. 4 and 4a. FIG. 4 illustrates yet another IOL which includes an optic 412 and a fixation member each of the components of another 414. Except as expressly stated herein, each of the components of another IOL 410 is structured and is sized and functions in a manner similar to the corresponding components of IOL 10. The reference numerals of the corresponding components of yet another IOL 410 are increased by 400 relative to the reference numerals of the corresponding components of IOL 10.

The primary difference between IOL 410 and IOL 10 is that fixation member 414 is structured to include a relatively thick portion 60 and a relatively thin or reduced thickness portion 62. Portion 62 has a reduced maximum thickness in a direction generally parallel to the optical axis 415 relative to the maximum thickness of portion 60. Reduced thickness portion 62 is sufficiently thin that it can be broken, for example, by a laser beam, at substantially any point along its length, without breaking or otherwise detrimentally affecting portion 60. By passing a laser beam through the pupil of the eye, the reduced thickness portion 62 of the fixation member 414 can be broken or otherwise compromised, thereby reducing the strength of fixation member 414. In so doing, the position of optic 412 is controllably changed to recenter the optic 412 relative to the pupil of the eye. One very advantageous feature of fixation member 414 is that the reduced thickness portion 62 extends over a relatively large part of the total length of fixation member 414. This allows the surgeon to choose over a relatively broad range where the fixation member 414 is to be altered to achieve the desired repositioning of the optic 414. This provides an additional degree or amount of control in repositioning optic 414.

FIGS. 5 and 5a illustrate a still further IOL 510 in accordance with the present invention. Except as expressly stated herein, each of the components of still further IOL 510 is structured and is sized and functions in a manner similar to the corresponding components of IOL 10. The reference numerals of the corresponding components of still further IOL 510 are increased by 500 relative to the reference numerals of the corresponding components of IOL 10.

IOL 510 is quite similar to IOL 410 except that the area of reduced thickness portion 66 generally parallel to the optical axis 515 of optic 512 is located outwardly from the thick portion 64 of fixation member 514. Having the portion of reduced thickness 66 located outwardly relative to the thick portion 64 allow reduced thickness portion 66 to be longer and, therefore, provide some additional amount of choice in deciding where along reduced thickness portion 66 is fixation member to be altered.

FIG. 6 illustrates IOL 610 in accordance with the present invention. Except as expressly stated herein, IOL 610 is structured and is sized and functions in a manner similar to the corresponding components of IOL 10. The reference numerals of the corresponding components of further additional IOL 610 are increased by 600 relative to the reference numerals of the corresponding components of IOL 10.

IOL 610 includes an optic 612 and a fixation member 614. Fixation member 614 includes the first arm 70, a second arm 72 and a third arm 74 separated by hollow or through (open) spaces 76 and 78. First arm 70 is thinner than second arm 72, which, in turn, is thinner than third arm 74. Depending upon the amount of repositioning of optic 612 desired, first arm 70 or second arm 72 or third arm 74 can be broken by a laser beam. Alternately two of these arms can be broken to achieve the desired repositioning of optic 612.

While this invention has been described with respect to various specific examples and embodiments, it is to be understood that the invention is not limited thereto and that it can be variously practiced within the scope of the following claims.

What is claimed is:

1. An intraocular lens comprising an optic and, secured to said optic, a fixation member including a distal end extending away from said optic and first and second spaced apart arms secured to said optic, located proximally of said distal end and respectively having substantially different cross sectional areas, one of said first and second arms structured to be altered after said intraocular lens is placed in an eye to at least assist in controllably repositioning said optic substantially perpendicular to the optical axis of the eye.

2. The intraocular lens of claim 1 wherein one of said first and second arms is structured to be altered non-surgically after said intraocular lens is placed in an eye to at least assist in controllably repositioning said optic substantially perpendicular to the optical axis of the eye and said fixation member is effective after one of said first and second arms is altered.

3. The intraocular lens of claim 1 wherein one of said first and second arms is structured to be broken non-surgically after said intraocular lens is placed in an eye to at least assist in controllably repositioning said optic substantially perpendicular to the optical axis of the eye.

4. The intraocular lens of claim 1 which is structured to be placed into the posterior chamber of the eye, and wherein one of said first and second arms is structured to be altered by energy passed through the pupil of the eye.

5. The intraocular lens of claim 1 wherein said first and second arms comprise a polymeric material having a glass transition temperature of at least about 40° C.

6. The intraocular lens of claim 1 wherein one of said first and second arms is structured to be altered after said intraocular lens is placed in an eye having a pupil to at least assist in controllably centering said optic relative to the pupil of the eye.

7. An intraocular lens comprising an optic having an optical axis and, secured to said optic, a fixation member including a distal end extending away from said optic and first and second spaced apart arms secured to said optic, located proximally of said distal end, one of said first and second arms having an area of substantially reduced cross section relative to the overall cross section of the arm in which said area is located, said area being structured to be altered after said intraocular lens is placed in an eye so that said altering results in a substantially predetermined amount of repositioning of said optic substantially perpendicular to the optical axis of the eye.

8. The intraocular lens of claim 7 wherein said area is structured so that altering said area results in a substantially predetermined amount of centering of said optic relative to the pupil of the eye.

9. The intraocular lens of claim 7 wherein said area is structured to be altered non-surgically after said intraocular lens is placed in an eye having a pupil to at least assist in controllably centering said optic relative to the pupil of the eye and said fixation member is effective after said area is altered.

10. The intraocular lens of claim 7 wherein said area is structured to be broken non-surgically after said intraocular lens is placed in an eye to at least assist in controllably centering said optic relative to the pupil of the eye.

11. The intraocular lens of claim 7 which is structured to be placed into the posterior chamber of the eye, and wherein said area is structured to be altered by energy passed through the pupil of the eye.

12. The intraocular lens of claim 7 wherein said area comprises a polymeric material having a glass transition temperature of at least about 40° C.

13. An intraocular lens comprising an optic and, secured to said optic, an elongated fixation member including a distal end extending away from said optic and a proximal portion defining a first hollow space and a second hollow space located adjacent said first hollow space and separated from said first hollow space by an alterable portion structured to be altered after said intraocular lens is placed in an eye to at least assist in controllably repositioning said optic substantially perpendicular to the optical axis of the eye.

* * * * *